United States Patent [19]

Hoffmann et al.

[11] Patent Number: 4,908,481

[45] Date of Patent: Mar. 13, 1990

[54] PREPARATION OF 1-(4-HYDROXY-PHENYL)-BUTAN-3-ONE AND NOVEL INTERMEDIATES

[75] Inventors: Werner Hoffmann, Neuhofen; Dieter Degner, Dannstadt-Schauernheim, both of Fed. Rep. of Germany

[73] Assignee: BASF Aktiengesellschaft, Ludwigshafen, Fed. Rep. of Germany

[21] Appl. No.: 798,361

[22] Filed: Nov. 18, 1985

Related U.S. Application Data

[63] Continuation of Ser. No. 250,935, Apr. 6, 1981, abandoned.

[30] Foreign Application Priority Data

Apr. 22, 1980 [DE] Fed. Rep. of Germany ....... 3015359

[51] Int. Cl.$^4$ ............................................ C07C 49/248
[52] U.S. Cl. .................................. 568/308; 568/313; 568/316
[58] Field of Search .................. 568/308, 313, 316

[56] References Cited

U.S. PATENT DOCUMENTS

| | | | |
|---|---|---|---|
| 3,098,874 | 7/1963 | Porsch et al. | 568/308 |
| 3,420,853 | 1/1969 | Moed et al. | 568/308 |
| 3,928,421 | 12/1975 | Kyogoku et al. | 568/313 |
| 3,997,608 | 12/1976 | Suh | 568/308 |
| 4,062,978 | 12/1977 | Cole et al. | 568/308 |
| 4,218,468 | 8/1980 | Paul | 568/313 |
| 4,271,319 | 6/1981 | Tang et al. | 568/313 |
| 4,290,974 | 9/1981 | Bouillon et al. | 568/313 |

FOREIGN PATENT DOCUMENTS

| | | | |
|---|---|---|---|
| 702894 | 2/1941 | Fed. Rep. of Germany . | |
| 1098951 | 7/1958 | Fed. Rep. of Germany . | |
| 2145308 | 3/1973 | Fed. Rep. of Germany | 568/303 |
| 1094417 | 7/1966 | United Kingdom | 568/313 |

OTHER PUBLICATIONS

McOmie, "Protective Groups in Organic Chem.", pp. 157–167 (1973), Blenun Press.
Papa et al., I.A.C.S., Vol. 70, pp. 3358–3360 (1948).
House, Modern Synthetic Reactions, pp. 632–642 (1972).
Houben-Weyl, Methoden Der Organischen Chemie, Band VI/lc, Phenole, p. 316 (1976)

*Primary Examiner*—James H. Reamer
*Attorney, Agent, or Firm*—Oblon, Spivak, McClelland, Maier & Neustadt

[57] ABSTRACT

A simple process for preparing 1-(4-hydroxy-phenyl)-butan-3-one, a sought-after natural aromatic, in a pure form and in good yield from easily accessible starting materials, wherein a 4-tert-alkoxy-benzaldehyde is condensed, under alkaline conditions, to give a novel 1-(4-tert.-alkoxy-phenyl)-but-1-en-3-one, the latter is hydrogenated, during or after this condensation, to give a novel 1-(4-tert-alkoxy-phenyl)-butan-3-one, and isobutene or 2-methyl-but-1(2)-ene is eliminated from this compound in the presence of a catalytic amount of an acid. The novel intermediates have the general formula t,10 where R is H or $CH_3$ and the broken line may or may not be an additional carbon-carbon bond.

10 Claims, No Drawings

PREPARATION OF 1-(4-HYDROXY-PHENYL)-BUTAN-3-ONE AND NOVEL INTERMEDIATES

This application is a continuation of application Ser. No. 250,935, filed Apr. 6, 1981.

The present invention relates to a process for the preparation of 1-(4-hydroxy-phenyl)-butan-3-one and to novel intermediates for this process, namely 1-(4-tert.-alkoxy-phenyl)-butan-3-one derivatives and -but-1-en-3-one derivatives of the general formula III

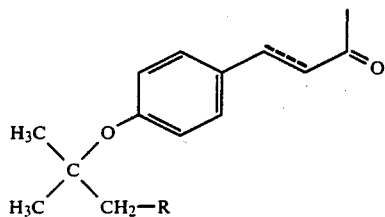

where R is H or CH$_3$, preferably H, and the broken line may or may not be an additional carbon-carbon bond.

1-(4-Hydroxy-phenyl)-butan-3-one is a sought-after natural aromatic, referred to as raspberry ketone or frambione. There have, therefore, been many attempts to find an advantageous method of preparing this compound.

The most important prior art processes for its preparation entail alkylating phenol with methyl vinyl ketone or a derivative thereof in the presence of an acidic catalyst (cf. German Patent 2,145,308). Disadvantages of this process are unsatisfactory yields and the need for expensive purification in order to achieve the requisite quality of aroma, since the high reactivity of the starting material causes the formation of substantial amounts of by-products.

It has also been disclosed that 4-hydroxy-benzaldehyde can be condensed with acetone to give 4-hydroxy-benzalacetone, which is then hydrogenated to 4-(4-hydroxy-phenyl)-butan-2-one (cf. J. Am. Chem. Soc. 70 (1948), 3360). The 4-hydroxy-benzaldehyde required as the starting compound for this two-stage process is, however, difficult to prepare and therefore very expensive. Furthermore, the overall yield of 1-(4-hydroxy-phenyl)-butan-3-one obtained by this process is unsatisfactory.

According to British Patent 1,094,417, raspberry ketone is obtained by reacting p-methoxy-benzyl chloride with ethyl acetoacetate in the presence of potassium carbonate and cleaving the resulting 1-(p-methoxy-phenyl)-butan-3-one with concentrated hydrobromic acid solution. As is shown by Example 2 of the said patent, the cleavage of the methyl ether with HBr is incomplete and consequently adds substantially to the difficulty of isolating the desired raspberry ketone. Furthermore, the handling of hydrogen bromide and of the methyl bromide liberated involves expensive apparatus.

It is an object of the present invention to provide a process by means of which raspberry ketone is obtained simply, in a very pure form and in good yield, from easily obtainable starting compounds.

We have found that this object is achieved by a process for the preparation of 1-(4-hydroxy-phenyl)-butan-3one (I), wherein A. a corresponding 4-tert.-alkoxy-benzaldehyde of the general formula II

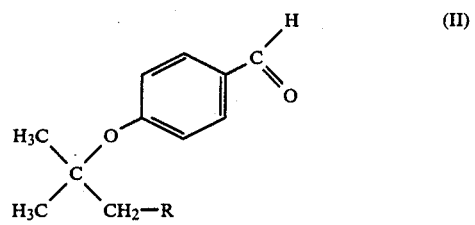

where R is H or CH$_3$, is condensed with acetone under alkaline conditions to give the novel 1-(4-tert.-alkoxy-phenyl)-but-1-en-3-one of the general formula IIIa

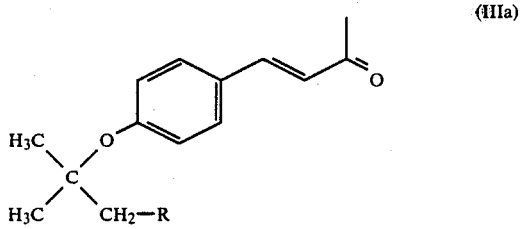

B. the latter is hydrogenated, during or after this condensation, to give the novel 1-(4-tert.-alkoxy-phenyl)-butan-3-one of the formula IIIb

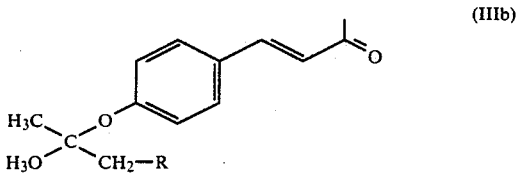

and

C. isobutene or 2-methyl-but-1(2)-ene is eliminated therefrom, at from 40° to 150° C., in the presence of a catalytic amount of an acid.

The invention also relates to the novel intermediates, of the general formula III (IIIa and IIIb), for this process.

Surprisingly, the process of preparation according to the invention, employing the novel intermediates, substantially overcomes all disadvantages of the conventional processes. Thus, for example, the 4-tert.-alkoxy-benzaldehydes of the formula II, required as starting materials, are nowadays obtainable easily and in good yields. For example, they can be prepared, according to German Laid-Open Application DOS . . . (German Patent Application P 29 35 398.8), which does not constitute a prior publication, by electrochemical oxidation of p-tert.-butoxy-toluene in the presence of an alcohol, followed by acetal cleavage.

In contrast to the starting materials and intermediates employed in the condensation of p-hydroxy-benzaldehyde (in which, in addition, not less than molar amounts of alkali are lost through phenolate formation), the novel starting materials and intermediates are not solids but liquids, which substantially simplifies the procedure, especially on an industrial scale. The novel intermediates IIIa and IIIb can be obtained in 99% purity in a simple manner, namely by distillation. The tert.-alkyl groups are not split off under the distillation conditions.

Both the condensation with acetone and the hydrogenation proceed simply and with good yields. The elimination of the protective group of the phenol, which can be carried out with traces of acid in aqueous suspension, proves particularly advantageous and leads to a crystalline product which after a single recrystallization is 99% pure.

The reaction of the 4-tert.-alkoxy-benzaldehyde of the formula II with acetone is carried out in a conventional manner, in a basic medium. In general, from 1 to 10, especially from 3 to 6, moles of acetone are employed per mole of aldehyde. Suitable catalysts are alkali metal hydroxides and alkaline earth metal hydroxides as well as alkali metal alcoholates and alkaline earth metal alcoholates. Per mole of aldehyde, from 0.0001 to 0.1, especially from 0.001 to 0.01, mole of catalyst is employed. The reaction can be carried out in the presence or absence of an inert solvent or diluent, batchwise or continuously. Reaction temperatures of from 0° to 50° C., especially from 15° to 35° C., have proved advantageous. The course of the reaction can be followed by thin layer chromatography or gas chromatography. After completion of the reaction, the catalyst is neutralized with an inorganic or organic acid and the resulting 1-(4-tert.-alkoxy-phenyl)-but-1-en-3-one of the formula IIIa is isolated by distillation after conventional working-up.

The hydrogenation of the but-1-en-3-one of the formula IIIa can be carried out in a conventional manner, in the absence of a solvent, or in an inert solvent such as methanol, ethyl acetate or tetrahydrofuran. Suitable catalysts are the conventional hydrogenation catalysts, amongst which palladium or platinum catalysts on carriers such as active charcoal, silica gel or aluminum oxide are preferred.

The reaction temperature may be from room temperature to 150° C. and the hydrogen pressure from atmospheric pressure to 50 bar. The 1-(4-tert.-alkoxy-phenyl)-butan-3-one of the formula IIIb is in general isolated by filtration followed by distillation.

The direct reaction of the benzaldehyde of the formula II with acetone and hydrogen to give the butanone IIIb is carried out with the aid of a mixed catalyst. Suitable catalysts are zinc oxide, aluminum oxide and active charcoal, which are modified with copper, nickel, cobalt, palladium or platinum. A catalyst system which contains an oxide or salt of a rare earth metal together with a metal of group VIII of the periodic table of the elements is also advantageous; such systems are described in German Patent 2,615,308. The reaction temperature is from 150° to 250° C. and the pressure from 10 to 50 bar.

The protective group of the phenol can be eliminated with an aqueous acid, such as sulfuric acid, phosphoric acid, hydrochloric acid, formic acid, acetic acid or the like. Catalytic amounts of the acid, ie. from about 0.001 to 0.5 mole per mole of IIIb, suffice. In general, the elimination is effected at from 40° to 150° C., preferably from 50° to 110° C. Solvents are generally not required and the reaction is advantageously carried out in aqueous suspension. By proceeding in this way, the product can, after completion of ether cleavage, by isolated in a crystalline form which is about 95% pure. This material can then be brought to about 99% purity by a single recrystallization from ethanol/water or methyl tert.-butyl ether.

The isobutylene or 2-methyl-but-1(2)-ene liberated by the cleavage reaction can be re-used to prepare the p-tert.-alkoxy-toluene.

Using the process according to the invention, the sought-after aromatic 1-(4-hydroxy-phenyl)-butan-3-one can be prepared in a simple manner, in a pure form and with good yields, from readily obtainable starting materials. It is only through the novel compounds IIIa and IIIb that this advantageous process becomes feasible. The butenes IIIa, by virtue of their ultraviolet absorption at from 300 to 310 nm, are also useful as light-protecting agents possessing a filter effect in the ultraviolet-B region (e.g. as anti-sunburn agents).

EXAMPLE 1

(a) Preparation of 1-(4-tert.-butoxy-phenyl)-but-1-en-3-one 89 g (0.5 mole) of p-tert.-butoxy-benzaldehyde are added dropwise, in the course of 15 minutes, to a mixture of 290 g (5 moles) of acetone and 30 ml of 0.5% strength aqueous sodium hydroxide solution at 20°–25° C., whilst stirring. After all has been added, the pH must be not less than 10; if it is not, sodium hydroxide solution must then be added. The reaction is complete after about 5 hours, as is demonstrable by thin layer chromatography or gas chromatography. Acetic acid is then added to the solution until it is neutral, the excess acetone is distilled off under reduced pressure and the reaction product is taken up in ether. The ether solution is washed salt-free with water, the ether is distilled off and the reaction product is fractionated, giving 88 g of main fraction. This corresponds to a yield of 81% of theory.

Boiling point: 17°–120° C./0.01 mbar; $n_D^{25}=1.5689$; UV spectrum: $E_{1\ cm}^{1\%}$ at $\lambda_{max}$ 305 nm: 896.

(b) Preparation of 1-(4-tert.-butoxy-phenyl)-butan-3-one 3 g of an 0.5% strength palladium/aluminum oxide catalyst in powder form are added to 109 g (0.5 mole) of 1-(4-tert.-butoxy-phenyl)-but-1-en-3-one prepared as described in (a), and the compound is hydrogenated at 100° C. and 10 bar hydrogen pressure until no further hydrogen is taken up. The catalyst is then filtered off and the reaction product is fractionated, giving 101 g of main fraction (yield: 92% of theory).

Boiling point: 114°–116° C./0.01 mbar; $n_D^{25}=1.4981$.

(c) Preparation of 1-(4-hydroxy-phenyl)-butan-3-one 100 g (0.45 mole) of 1-(4-tert.-butoxy-phenyl)-butan-3-one are suspended in 250 ml of 2N sulfuric acid and the mixture is refluxed for about 3 hours, with vigorous stirring. The course of the reaction can be followed by measuring the isobutylene liberated. After completion of the reaction, the mixture is cooled to room temperature and brought to pH 6 with dilute sodium hydroxide solution, after which the product crystallizes out in about 95% purity. It is isolated by filtering off or centrifuging (73 g of 95% pure material; yield 93%), and is recrystallized from water/ethanol.

Solidification point: 83°–85° C.

EXAMPLE 2

Preparation of 1-(4-tert.-butoxy-phenyl)-butan-3-one 58 g (1 mole) of acetone and 36 g (0.2 mole) of p-tert.-butoxy-benzaldehyde are introduced into a 300 ml stirred autoclave, 5 g of zinc oxide and 1 g of 1% strength palladium on active charcoal are added and the mixture is heated to 160° C., with vigorous stirring, under 20 bar hydrogen pressure. After a reaction time of 2 hours, the reaction mixture is cooled, freed from catalyst by filtration, and subjected to fractional distillation. 19 g of 1-(4-tert.-butoxy-phenyl)-butan-3-one (yield: 43%) are obtained.

EXAMPLE 3

(a) Using a method similar to that of Example 1a, 290 g (5 moles) of acetone, 30 ml of an 0.5% strength aqueous sodium hydroxide solution and 96 g (0.5 mole) of p-tert.-amyloxy-benzaldehyde are used to prepare 1-(4-tert.-amyloxy-phenyl)-but-1-en-3-one. Boiling point = 135° C./0.01 mbar; $n_D^{25} = 1.5648$; UV spectrum: $E_{1\ cm}^{1\%} = 886$ at $\lambda_{max}$ 311 nm (in isopropanol)

(b) Following a method similar to that described in Example 1b, 116 g (0.5 mole) of 1-(4-tert.amyloxy-phenyl)-but-1-en-3-one, prepared as described in Example 3a, are used to prepare 1-(4-tert.-amyloxy-phenyl)-butan-3-one. Boiling point = 128°–129° C./0.01 mbar; $n_D^{25} = 1.4894$.

We claim:

1. 1-(4-tert.-Alkoxy-phenyl)-butan-3-one and -but-1-en-3-one derivatives of the general formula III

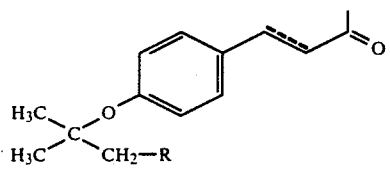

(III)

where R is H or CH₃ and the broken line may or may not be an additional bond between the carbon atoms which it links.

2. A process for the preparation of 1-(4-hydroxyphenyl)-butan-3-one, comprising:

(a) preparing a compound of the formula:

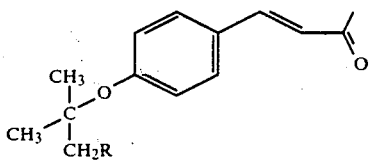

wherein R is H or CH₃ by condensing acetone under alkaline conditions with a compound of the formula:

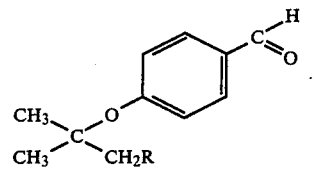

II (b) hydrogenating compound IIIa after or while it is formed thereby yielding a compound of the formula:

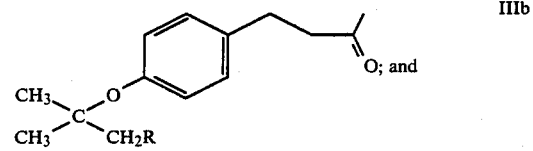

IIIb (c) eliminating isobutene or 2-methyl-but-1(2)-ene from compound IIIb at a temperature of 40° to 150° C. in the presence of an acid.

3. The process of claim 2, wherein the molar ratio of acetone to benzaldehyde reactant ranges from 1–10:1.

4. The process of claim 2, wherein said condensation reaction between said benzaldehyde compound and acetone is conducted in the presence of a catalyst selected from the group consisting of alkali metal hydroxides, alkaline earth metal hydroxides, alkali metal alcoholates, and alkaline earth metal alcoholates.

5. The process of claim 4, wherein said catalyst is present in an amount of 0.0001–0.1 mole per mole of aldehyde reactant.

6. The process of claim 2, wherein said condensation reaction is conducted at a temperature of from 0° to 50° C.

7. The process of claim 2, wherein said hydrogenation step is conducted over a palladium or platinum catalyst supported on active charcoal, silica gel or aluminum oxide.

8. The process of claim 2, wherein said acid is selected from a group consisting of aqueous sulfuric acid, aqueous phosphoric acid, aqueous hydrochloric acid, aqueous formic acid and aqueous acetic acid.

9. The process of claim 8, wherein the amount of acid present ranges from 0.001 to 0.5 moles per mole of compound IIIb.

10. The process of claim 2, wherein in step (b) of said process, said compound IIIa is hydrogenated after it is formed.

* * * * *